United States Patent [19]

Chaudhuri et al.

[11] Patent Number: 5,427,774
[45] Date of Patent: Jun. 27, 1995

[54] HETEROCYCLIC QUATERNARY SALTS OF PARA-DIALKYLAMINO BENZAMIDE DERIVATIVES

[75] Inventors: Ratan K. Chaudhuri, Butler; Anatoly Alexander, Berkeley Heights; Anna A. Gripp, Whippany, all of N.J.

[73] Assignee: ISP Van Dyk Inc., Belleville, N.J.

[21] Appl. No.: 356,616

[22] Filed: Dec. 15, 1994

Related U.S. Application Data

[63] Continuation-in-part of Ser. No. 111,690, Aug. 25, 1993.

[51] Int. Cl.$^6$ .......................... A61K 7/06; A61K 7/42; C07D 263/04
[52] U.S. Cl. ......................... 424/60; 424/47; 424/70.9; 514/938; 544/165; 546/221; 548/215
[58] Field of Search ............... 424/60, 70, 47; 514/938; 548/215; 544/165; 546/221

[56] References Cited

U.S. PATENT DOCUMENTS

| | | | |
|---|---|---|---|
| 3,878,229 | 4/1975 | Strobel | 424/60 X |
| 3,879,443 | 4/1975 | Strobel | 424/60 X |
| 4,061,730 | 12/1977 | Kalopissis et al. | 424/59 |
| 4,069,309 | 1/1978 | Ciaudelli et al. | 424/60 X |
| 4,256,664 | 3/1981 | Epstein et al. | 424/60 X |
| 4,680,144 | 7/1987 | Conner | 424/60 X |
| 5,078,990 | 1/1992 | Martin et al. | 424/70 |

OTHER PUBLICATIONS

The Merck Index, 10th Ed., (1983), p. 1116, item 7658.
Steen, et. al., C.A., 118:51841 (1992).
Kimura, et. al., C.A., 109:31538 (1988).
Schanker, et. al., C.A., 104:61509 (1986).
Easton, et. al., C.A., 89:208 889 (1978).

Primary Examiner—Joseph Paul Brust
Attorney, Agent, or Firm—Marilyn J. Maue; Joshua J. Ward

[57] ABSTRACT

This invention relates to non-hydrolyzable, non-irritating, hair, skin and textile substantive quaternary ammonium salts of a para-dialkylamino benzamide having the formula

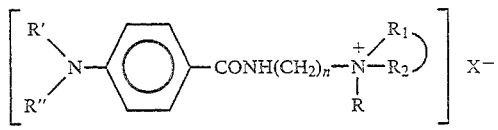

wherein R' and R'' are each selected from the group of $C_1$ to $C_2$ alkyl; n is an integer having a value of from 2 to 6; R is an alkyl radical having from 1 to 30 carbon atoms; $R_1$ and $R_2$ together with the attached cationic nitrogen atom forms a 5 to 6-membered heterocyclic ring containing a hetero oxygen atom in addition to the heteronitrogen atom and is selected from the group of

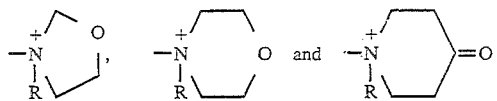

and X is an anion. These benzamide heterocyclic derivatives are active sunscreening agents which are usefully employed at a concentration of from about 0.5 to about 10 wt. % in a formulation requiring protection against the harmful effects of sunlight, such as skin burn, hair damage, color fading, etc.

16 Claims, No Drawings

HETEROCYCLIC QUATERNARY SALTS OF PARA-DIALKYLAMINO BENZAMIDE DERIVATIVES

This application is a continuation-in-part of Ser. No. 08/111,690, filed Aug. 25, 1993.

In one aspect the present invention relates to novel substantive compounds for skin, hair, paints, textiles and fibers of wool, cotton, silk and synthetics which provide protection from the undesirable affects of sunlight. In another aspect the invention relates to the use of such compounds as sunscreens in personal care or in other formulations.

BACKGROUND OF THE INVENTION

In addition to the recognized detrimental affects of sunlight on printed or colored fabrics and painted surfaces, human hair damage caused by sunlight in the ultraviolet spectrum is more severe than that resulting from all other factors such as weather, wind, atmospheric pollution, salt water, chlorinated water, perming, coloring, bleaching and improperly applied or repetitive treatments. Notwithstanding the need for effective sunscreens, none have been developed which provide desired hair substantivity while avoiding other deleterious changes in structure, brittleness, hair softness and the like. Prior attempts to remedy these problems have proven unsatisfactory. For example, U.S. Pat. Nos. 3,879,443; 3,878,229; 4,069,309 and 4,680,144 disclose various sunscreens dependent on an ester functionality. However, these compounds tend to be hydrolytically unstable to the extent that the formulator must avoid conditions conducive to hydrolysis during formulation. Also, since these esters lack hydrogen bonding capability with skin protein or hair keratin, their hair substantivity is not satisfactory.

U.S. Pat. No. 4,256,664 proposes several p-substituted aromatic amines or nitro containing sunscreens having an amide functionality and optionally containing a hydroxy substituent. However, the primary amines of this patent oxidize rapidly in air, thereby altering desired hair color and, in some instances, form nitroso amines some of which are known carcinogens. Additionally, the primary amines and nitro compounds are recognized skin irritants. Further, the amine compounds are subject to intermolecular and solvent hydrogen bonding which characteristic causes a significant shift in UV maxima absorption and reduces absorption in the desired spectrum range.

M. F. Saettone et al. in THE INTERNATIONAL JOURNAL OF COSMETIC SCIENCE, Vol. 8, 9–25, 1986, describes types of amido quaternaries based on salicyclic and cinnamic acids. The salicylamides are ortho substituted with spatial arrangements permitting internal molecular hydrogen bonding. The ortho relationship of the phenolic group to the bulky amide group causes steric hindrance and stress within the molecule. To counter this steric effect, the groups which deviate slightly from planarity are present. However, any minor deviation from planarity causes a reduction in the extinction coefficient and hence a corresponding reduction in the efficacy of protection against harmful sun rays. On the other hand, cinnamoylamides have additional unsaturation and conjugation with respect to both the aromatic ring and the carbonyl group. This structure permits electron delocalization to take place within the molecule; but, although the energy corresponding to this electron transition corresponds to a desired wavelength of about 305 nm, the molar extinction coefficient is materially lower than that for the corresponding para-dimethylamino carbonyl analog. Finally, the cinnamoyl compounds are subject to cis-trans isomerization as well as to oxidative cleavage and polymerization, i.e. characteristics to be avoided for effective sunscreens.

Still another patent, U.S. Pat. No. 4,061,730, seeks to remedy the above problems by the use of quaternized benzylidene camphor sunscreens. However, since quaternization eliminates conjugation in the compound, the sun protection efficiency is significantly reduced.

From the above discussion, it will be appreciated that the discovery of a commercially viable and hair substantive sunscreen is remote.

Other heterocyclic quaternary salts of pdialkylamino benzamide derivatives which are effective substantive compounds for personal care and other commercial uses are covered in patent application Ser. No. 08/111,690, filed Aug. 25, 1993 by Ratan K. Chaudhuri et al.

It is an object of the present invention to provide an effective, non-irritating sunscreening agent which is not subject to hydrolysis, which has high substrate substantivity and which is an alternative to the compounds claimed in Ser. No. 08/111,690 [ibid].

Another object of the invention resides in the synthesis of said sunscreening agent.

Still another object is to provide a novel water insoluble sunscreening agent for extended use in hair care.

These and other objects will become apparent from the following description and disclosure.

THE INVENTION

In accordance with the present invention, a substantially water insoluble, non-irritating and hydrolysis resistant cationic sunscreening agent is provided which possesses high molecular planarity and which is easily incorporated into commercial formulations to provide stable compositions.

The present benzamide derivatives can be employed to prevent color alteration in paints or painted substrates, e.g. automotive vehicles and mono or multi colored textile fabrics, and the like. Because of their high hair, skin and wool substantivity, the present compounds are particularly useful in cosmetic applications, as in hair conditioning shampoos, silicone containing softeners, hair conditioners and rinses, styling mousses, gels or lotions, hair sprays, hair dyes and bleaching compositions. Since the present compounds interact with hair protein, they provide UV protection and conditioning properties long after hair treatment. Beneficial cosmetic applications also include their compatability and easy incorporation into skin care compositions, such as sun protection creams and lotions to inhibit skin ageing, wrinkle formation, erythema and carcinogenesis as well as in nail polish, lipstick, rouge or make-up bases. The benzamide derivatives of this invention also reduce fading of natural and synthetic dyes and minimize or eliminate photodegradation in dyed and undyed cotton, linen, silk and wool fabrics as well as color alteration in paints and painted surfaces exposed to climatic conditions as in automotive and house paints.

The non-hydrolyzable, non-irritating, substantive derivatives of this invention are quaternary ammonium salts of a para-dialkylamino benzamide compound having the formula

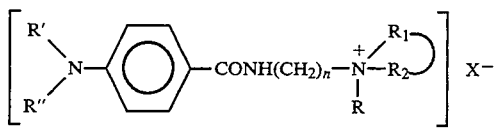

wherein R' and R'' are each selected from the group of $C_1$ to $C_2$ alkyl; n is an integer having a value of from 2 to 6; R is a linear, branched or cyclic alkyl radical having from 1 to 30 carbon atoms; $R_1$ and $R_2$ together with the attached cationic nitrogen atom forms a 5 to 6-membered heterocyclic ring containing a hetero oxygen atom in addition to the heteronitrogen atom and are selected from the group of

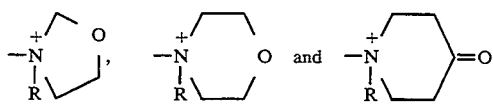

described as morpholinyl, oxazolidinyl and morpholonyl radicals, respectively and X is an anion, preferably selected from the group of chloride, bromide, sulfate, sulfonate, haloacetal and aryl sulfonates.

Of the above benzamide compounds, preferred are those wherein n has a value of 2 to 4; R is alkyl having 10 to 20 carbon atoms. It is to be understood that mixtures of the present benzamides can be employed in a composition to provide combined UV protection.

The present compounds are unique in that they absorb UV in wavelengths of from about 280 to about 330 nm and possess a molecular extinction coefficient of up to about 30,000. The present compounds are generally compatible with any composition requiring UV protection and can be added in an effective amount of between about 0.5 and about 10 wt. %, preferably between about 1 and about 3 wt. %, based on total composition.

Solutions of the present compounds are also usefully applied as a separate coating over a treated substrate. For example, a vehicle or aircraft can be sprayed or brushed, with a 2 to 10% solution of the present compound dissolved in a suitable solvent such as fatty alcohols, e.g. octyldodecanol, isocetyl alcohol, alkyl lactates containing 12 to 18 carbon atoms, 2-ethylhexyl p-dimethylamino benzoate (Padimate O), etc. The compound can also be pressed into a cosmetic cake as in a cake powder for application to the skin.

The benzamides of the present invention are easily synthesized according to the following two-stage reaction

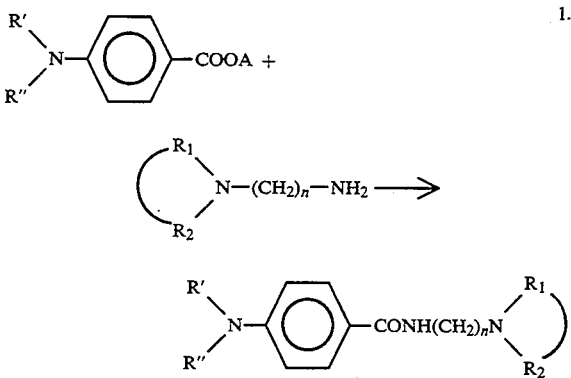

wherein A is $C_1$ to $C_8$ alkyl and the quaternizing agent is halogen, an anion forming organic moiety, e.g. alkyl such as tolyl, alkyl sulfonate, etc.

Stage 1 of the reaction is carried out at a temperature of between about 90° and about 180° C., preferably under reflux conditions for continuous removal of the alkanol by-product. The reaction of the aminobenzoate with the diamine is conducted in the presence of a base catalyst such as dimethyl formamide, triethanol amine, N-methyl-morpholine, hexamethylene tetraamine, dimethylamino-2-hydroxy propane, 2,4,6-tris(dimethylaminomethyl)phenol, potassium t-butoxide, KOH, NaOH, $NaOCH_3$, $NaOC_2H_5$ and the like. Between about 0.1 and about 24 hours, in the presence of from about 0.5 to about 2 weight % of the base catalyst, is sufficient to complete the reaction to the heterocyclic aminobenzamide product in a high yield greater than 96%. Preferred conditions for this stage of the reaction include a temperature of from about 120° to about 170° C. for a period of between about 1 and about 5 hours. The aminobenzoate and heterocyclic diamine can be reacted as a melt or in a 15–50%, preferably a 20–30%, solids solution or emulsion in a suitable liquid medium provided by, e.g. acetone, methyl ethyl ketone, ethyl acetate, cyclohexane, octane, xylene, toluene, etc. and mixtures thereof. Also, the reaction can be effected under a pressure sufficient to maintain a liquid phase when needed.

The quaternization stage is carried out at a temperature of between about 70° and about 140° C., preferably between 100° and 130° C., and is completed within a period of from about 10 minutes to about 24 hours, more often 1 to 6 hours, after which the product can be recovered by crystallization, from ethyl acetate or a similar solvent. Although the product can be recovered in crystalline form, these crystals may contain up to 10 wt. % water, more desirably between about 1 and about 8 wt. % water.

The quaternizing agents employed in the present invention include $C_1$ to $C_{30}$ alkyl- halide, sulfate, sulfonate, acetal and aryl sulfonates, e.g. p-tolyl sulfonate. The alkyl moiety of the quaternizing agent can be substituted with halogen and can be branched or linear. Preferred quaternizing agents are those containing from 12 to 20 carbon atoms in the alkyl moiety.

In the above reactions, equimolar amounts of the reacting species are preferred; however, ratios of from about 1:2 to about 2:1 may be employed in the second stage reaction.

Advantages of the present sunscreening agents are derived from the aromatic $-N(R)_2$ group, which unlike $-NH_2$, is stable, is not sensitive to pH changes present in various formulations, and is not oxidized in air. The substitution of —N(R)$_2$ in the para-position on the phenyl ring also eliminates H bonding with protic solvents which characterize the ortho —OH and —NH$_2$ phenyl substitutions of other sunscreens while the replacement of the ester linkage found in prior compounds with an amide linkage provides an additional binding site for the hair protein (keratin) through H-bonding. The presence of the heterocyclic quaternary amine group provides the salt linkage through the electrovalent union of the side chain acid keratin residues thereby imparting conditioning properties. All of the above factors in combination provide the synergistic effects and benefits of the present sunscreens.

Formulations containing the present quaternized heterocyclic amino-benzamide compounds can be used in pump or aerosol sprays.

The cosmetic formulations incorporating the present sunscreens generally include between about 40 and about 90 wt. % of a carrier or propellant such as deionized water, alcohol, isobutane or propane, etc., between about 10 and about 40 wt. % of a surfactant or surfactant mixture such as sodium and/or ammonium, lauryl sulfate, sodium laureth sulfate etc., and fragrance and/or coloring agent as desired.

These formulations may optionally contain between about 5 and about 50 % of one or more inert components including a film forming polymer such as a C$_1$ to C$_4$ ester of a methyl vinyl ether/maleic anhydride copolymer, a vinyl pyrrolidone/vinyl acetate copolymer, etc.; a preservative such as bronopol, an ester of p-hydroxybenzoic acid, 2-methyl-3(2H) isothiazolone, a mixture of methyl and propyl paraben, dimethyl-5,5-dimethylhydantoin, Germall® 115, imidazolidinyl urea, etc.; a sequestrant, and an antistatic agent.

Following compilation of formulations serves to illustrate the diversity of formula types currently available in the marketplace. In each of the formulations the sunscreen of the present invention is employed.

A. Formula type: FACE CREAM

| Ingredients | % w/w |
|---|---|
| Phase A | |
| Benzophenone-3 | 8.0 |
| Sunscreen | 6.0 |
| Cyclomethicone | 10.0 |
| Glyceryl stearate SE | 5.0 |
| Phenyldimethicone | 2.0 |
| Cetearyl alcohol (and) ceteareth-20 | 2.0 |
| Cetyl alcohol | 1.0 |
| Octyl palmitate | 10.0 |
| Phase B | |
| Water | QS |
| Preservative | QS |
| Glycerine | 5.0 |
| Diethanolamine p-methoxycinnamate | 8.0 |
| Titanium dioxide | 3.0 |
| Xanthan | 0.2 |
| Hydroxyethylcellulose | 0.1 |
| Phase C | |
| Fragrance | 0.3 |

B. Formula type: w/o WATER-RESISTANT CREAM

| Ingredients | % w/w |
|---|---|
| Phase A | |
| Mineral oil (and) lanolin alcohol | 5.0 |
| Isopropyl palmitate | 10.0 |
| Beeswax | 8.0 |
| Sorbitan sesquioleate | 2.0 |
| Mineral oil | 25.0 |
| Sunscreen | 6.0 |
| Benzophenone-3 | 4.0 |
| Phase B | |
| Water | QS |
| Borax | 0.4 |
| Preservative | QS |
| Propylene glycol | 5.0 |
| Phase C | |
| Fragrance | 0.25 |

C. Formula type: SUN BLOCK CREAM

| Ingredient | % w/w |
|---|---|
| Phase A | |
| Isopropyl myristate | 9.0 |
| Sunscreen | 10.0 |
| Benzophenone-3 | 5.0 |
| Menthyl anthranilate | 5.0 |
| Stearic acid XXX | 5.0 |
| Glyceryl monostearate | 6.0 |
| Cetyl alcohol | 5.0 |
| PEG-40 stearate | 2.0 |
| Phase B | |
| Water | QS |
| Xanthan | 0.3 |
| DEA-cetyl phosphate | 8.0 |
| Preservative | QS |
| Glycerine | 3.5 |
| Phase C | |
| Fragrance | 0.25 |

D. Formula type: WATER-PROOF LOTION Expected SPF: 15

| Ingredient | % w/w |
|---|---|
| Phase A | |
| Sunscreen | 8.0 |
| Benzophenone-3 | 4.0 |
| Myristyl myristate | 1.0 |
| Propylene glycol dipelargonate | 5.0 |
| Steareth-20 | 1.0 |
| Phase B | |
| Water | QS |
| Carbomer 1342 | 0.2 |
| Preservative | QS |
| Propylene glycol | 5.0 |
| Phase C | |
| PEG-15 cocamine | 0.2 |
| Phase D | |
| Fragrance | 0.25 |

E. Formula type: CATIONIC SUNSCREEN LOTION

| Ingredient | % w/w |
|---|---|
| Phase A | |
| Glycol stearate | 5.0 |
| C$_{12-15}$ alcohols benzoate | 3.5 |
| Sunscreen | 5.0 |
| PEG-40 stearate | 1.5 |
| Phase B | |
| Water | QS |
| Preservative | QS |
| Stearamidopropyl PG-dimonium chloride Phosphate | 3.5 |
| Glycerine | 4.0 |
| Phase C | |
| Fragrance | 0.3 |

F. Formula type: GREASELESS SUNSCREEN OIL

| Ingredient | % w/w |
|---|---|
| Benzophenone-3 | 3.0 |
| Sunscreen | 7.0 |
| Mineral oil | QS |
| Octyl palmitate | 15.0 |
| Fragrance | 0.3 |
| Sesame Oil | 1.0 |
| BHA | 0.1 |

G. Formula type: SUNSCREEN OIL
Comments: Octyl palmitate reduces oiliness of mineral oil while minimizing UV curve shift Expected SPF: 3

| Ingredient | % w/w |
|---|---|
| Sunscreen | 4.0 |
| Octyl palmitate | QS |
| Lauryl lactate | 15.0 |
| Mineral oil | 35.0 |

-continued

| Ingredient | % w/w |
|---|---|
| Isocetyl alcohol | 10.0 |
| Fragrance | 1.0 |

H. Formula type: LIP BALM STICK

| Ingredient | % w/w |
|---|---|
| Sunscreen | 7.0 |
| Benzophenone-3 | 3.0 |
| Castor oil | QS |
| Octyldodecanol | 5.0 |
| Beeswax | 15.0 |
| Ozokerite | 6.0 |
| Myristyl lactate | 4.0 |
| Candililla wax | 6.0 |
| Petrolatum | 5.0 |
| Fragrance | 0.5 |

I. Formula type: Water-resistant sunscreen mousse

| Ingredient | % w/w |
|---|---|
| Phase A | |
| Dimethicone | 10.0 |
| Sunscreen | 3.5 |
| Benzophenone-3 | 3.0 |
| Glyceryl PABA | 3.0 |
| Stearic acid XXX | 4.0 |
| Cetyl alcohol | 0.5 |
| Vitamin E acetate | 0.1 |
| Phase B | |
| Water | QS |
| Hydroxypropyl cellulose | 0.5 |
| Triethanolamine 99% | 0.5 |
| Ethanol | 20.0 |
| Preservative | QS |

J. Formula type: Sunscreen mousse

| Ingredient | % w/w |
|---|---|
| Water | QS |
| Propylene glycol | 5.0 |
| Quaternium-26 | 3.0 |
| Octyl methoxy cinnamate | 3.0 |
| Cetearyl alcohol (and) ceteareth-20 | 1.0 |
| Octyldodecanol | 5.0 |
| Preservative | QS |

K. Formula type: MAKE-UP MOUSSE

| Ingredient | % w/w |
|---|---|
| Phase A | |
| Glyceryl dilaurate | 2.5 |
| Glyceryl stearate SE | 3.0 |
| Cetyl alcohol | 1.5 |
| Decyl oleate | 2.5 |
| Propylene glycol depelargonate | 3.0 |
| Sunscreen | 3.5 |
| Phase B | |
| Water | QS |
| Hydroxyethylcellulose | 0.5 |
| Sorbitol 70% | 5.0 |
| Pigment | 15.0 |
| Preservative | QS |
| Phase C | |
| Ethanol | 20.0 |

L. Formula type: SUNSCREEN GELEE

| Ingredient | % w/w |
|---|---|
| Myristyl lactate | 5.0 |
| Tridecylneopentanoate | 10.0 |
| Sunscreen | 4.0 |
| Petrolatum | QS |
| Paraffin | 5.0 |
| Beeswax | 4.0 |
| Calcium stearate | 5.0 |
| Cetearyl alcohol | 2.0 |
| Fragrance | 1.0 |
| Preservative | QS |

M. Shampoo

| | Parts |
|---|---|
| Emersol 6400 (sodium lauryl sulfate) | 30.0 |
| Rewomid DC-212/S (Cocamide DEA) | 5.0 |
| Deionized water | 60 |
| Preservative | QS |
| Sunscreen | 4 |

Preparation: Heat all ingredients to 45–50° C.; cool to room temperature

N. Cream Rinse

| | | |
|---|---|---|
| A. | Stearalkonium chloride (50% solids) | 1.5 |
| | Sodium chloride | 0.1 |
| | Deionized water | 90.9 |
| | Sunscreen | 3.0 |
| B. | Emerest 2642 (polyethylene glycol 8 distearate) | 1.5 |
| | Ethoxyol AC (laneth-10 acetate) | 2.0 |
| | Preservative | |

Preparation: Heat both phases to 70° C.;
add A to B; cool to room temperature

O. Hair Conditioner

| | | |
|---|---|---|
| A. | Sunscreen | 2.0% |
| | Cetyl Alcohol | 2.0% |
| | Ethoxylated Sorbitan Esters | 4.0% |
| B. | Water | 92.0% |

Preparation: Heat both phases to 80° C.;
add A to B with stirring and continue for 1 hour.
Cool to room temperature.

P. Formulation of Hair Styling Mousse with Sun Protection

| | | |
|---|---|---|
| 1. | Water | 85.5% |
| 2. | Gafquat 755N | 2.0% |
| 3. | Ethoxylated Sorbitol Esters | 2.0% |
| 4. | Ethanol | 5.0% |
| 5. | Preservative | 1.0% |
| 6. | Sunscreen from Example 2 or 4 | 1.5% |
| 7. | Propellant | |
| | Dimethyl Ether | 4.0% |
| | n-Butane | 4.0% |

Q. Conditioning Shampoo Formulation, taken from Example 7 of U.S. Pat. No. 5,078,990, which are incorporated herein as representative teachings of suitable formulations for addition of the present sunscreens.

| ITEM | COMPONENT | WT. 5 |
|---|---|---|
| 1 | ammonium lauryl sulfate | 6.0 |
| 2 | ammonium laureth sulfate (1 mole EO) | 9.45 |
| 3 | sodium lauryl sulfate | 4.5 |
| 4 | distearyl dimethyl ammonium chloride (AROSURF ®) | 0.3 |
| 5 | distearyl phthalamic acid | 3.5 |
| 6 | sodium hydroxide | 0.085 |
| 7 | FD&C Blue #1 | 0.00024 |
| 8 | D&C yellow #10 | 0.0012 |
| 9 | tetrasodium EDTA/water softener | 0.2 |
| 10 | fragrance | 0.5 |
| 11 | DMDM hydantoin (GLYDANT ®) preservative | 0.1 |
| 12 | methyl & methylchloro isothiazolinone-preservatives | 0.05 |
| 13 | 33% SE-30 polysiloxane gum/67% SF96-350 polysiloxane oil | 2.5 |
| 14 | sunscreen | 0.8 |
| 15 | soft water | QS to 100 |

Add items #1, #2, and #3 and begin heating batch to 180° F.–185° F.

At 180° F. add item #4 and allow to completely mix in.

Add items #5, allow to mix in.

Add item #6, #7, and #8.

Allow to mix for 30 minutes at 180° F.–185° F.

After this time, samples should be cooled with item #15.

The conditioning agent (item 13) and sunscreen (14) then are added and mixed at a temperature of at least 30° C. and preferably at 40° C. to 50° C. The composition at this point exhibits lower frequency stretching bands at the higher temperatures and the conditioning agent is easily dispersed or dissolved within the emulsion without separation.

| | wt. % |
|---|---|
| Automotive Acrylic Enamel Components | |
| TiO₂ base containing 60% pigment | 220 |
| Color tinting base | 40 |
| Acrylic polymer (with pendant —OH and —COOH groups) 55% solids | 350 |
| Butoxy methylol melamine-formaldehyde resin - 55% solids | 230 |
| Butyl alcohol | 37 |
| Toluene sulfonic acid 50% in xylene | 2.6 |
| Xylene | 75.0 |
| Sunscreen | 5.4 |
| Propylene glycol methyl ether acetate | 40.0 |
| | 100.00 |
| Total solids 45 wt. % | |
| Pigment solids 25 wt. % | |
| Crosslinker of polymer 30% | |
| White Aircraft TopCoat | |
| 1:1 Aliphatic isocyanate-polyester polyol resin | 20.0 |
| TiO₂ (R960 Exterior grade) | 16.0 |
| Urethane catalyst | 2.0 |
| Flow/leveling/flood and float additives | 2.0 |
| Sunscreen | 10.0 |
| Mixture of methyl ethyl ketone, methyl isobutyl ketone and methyl allyl ketone | 50.0 |

Having generally described the invention, reference is now had to the accompanying Examples which illustrate preferred embodiments but which are not to be construed as limiting to the scope of the invention as more broadly defined above and in the appended claims.

EXAMPLE 1

Preparation of
N-(2-N-Morpholinoethyl)-p-dimethylamino benzamide

Ethyl-p-dimethylaminobenzoate (30.9 g, 0.16 mole), N-aminoethylmorpholine (25 g, 0.19 mole) and sodium methoxide (0.6 g) were introduced into a 3-neck, 100 ml glass reactor, equipped with stirrer, heater, nitrogen purge and deflegmator with a Dean-Stark device. The charged reactor was flushed with dry nitrogen for 15 minutes at ambient temperature and was then heated to 150° C. under vigorous stirring. After about 15 minutes accumulation of distillate, the reactor temperature was gradually increased to 170° C. in 5° increments over a period of 1 hour and was then maintained at 170° C. for a 23 additional hours.

The resulting mixture was then cooled to room temperature, washed with 300 ml of water and precipitated crystals recovered by filtration. These crystals were then suspended in another 200 ml of water and 30% of HCl was added to adjust the pH to 3. The resulting slurry was filtered, and filtrate was collected and treated with a suspension of sodium carbonate to pH 11. The precipitate was filtered, washed with water and allowed to dry. The dry crude product was then dissolved in methanol, insolubles were separated by filtration, and the remaining solution was evaporated to dryness in vacuo. The product yield was 24.7 g (56% of theoretical) of 98.5% pure product having a m.p. 154°–156° C.

A vacuum of about 10–20 mmHg was then applied to the product in the reactor which was heated to 90–95° C. for 30 minutes. The resulting distillate containing water and light products was discarded. The residue was cooled to room temperature and was identified by elemental analysis, ¹H and ¹³NMR and FTIR spectra, as N-(2-N-morpholinoethyl)-p-dimethylaminobenzamide. The product yield was 24.7 g (56% of theoretical based on ethyl-p-dimethylamino-benzoate).

EXAMPLE 2

Preparation of
Hexadecyl-[2-N-(p-dimethylaminobenzamido)ethyl]-Morpholinium p-toluenesulfonate N-(2-N-morpholinoethyl)-p-dimethylaminobenzamide (13.9 g, 0.09 mole) from Example 1 and 19.8 g of hexadecyl-p-toluenesulfonate (0.05 mole) were heated to 120° C. under a blanket of nitrogen with continuous stirring for 4 hours. The resulting melt was dissolved in 800 ml of hot ethylacetate and then crystallized from methyl ethyl ketone (100 ml) by cooling to ambient temperature. The crystals were recovered by filtration, dried in air and then under vacuum at 50°–60° C. The resulting crystals of hexadecyl-[2-(p-dimethylaminobenzamido)ethyl]morpholinium p-toluenesulfonate was recovered and the yield 13.7 g, was 41% of theoretical.

EXAMPLE 3

Preparation of
N-(2-N-Morpholonylpropyl)-p-dimethylamino benzamide

Ethyl-p-dimethylaminobenzoate (164.9 g, 0.85 mole), morpholonylaminopropylamine (95.9 g, 0.94 mole) and sodium methoxide (2.8 g, 0.054 mole) are introduced into a 4-neck, 500 ml glass reactor, equipped with stirrer, heater, nitrogen purge and deflegmator with a Dean-Stark device. The charged reactor is flushed with dry nitrogen for 15 minutes at ambient temperature and is then heated to 150° C. under vigorous stirring. After about 15 minutes accumulation of distillate, the reactor temperature is gradually increased to 180° C. in 5° increments over a period of 1 hour and is then maintained at 180° C. for an additional hour, whereupon a sample of the product is obtained.

The resulting mixture is then cooled to 95° C. and washed twice with 200 ml of hot water after which the aqueous phase is cooled to room temperature and precipitated crystals recovered by filtration. These crystals are then combined with the organic phase in the reactor.

A vacuum of about 10–20 mm Hg is applied to the product in the reactor which is heated to 90°–95° C. for 30 minutes. The resulting distillate containing water and light products is discarded. The residue is cooled to room temperature as the intermediate product of the process.

This product is converted to the quaternized p-toluene sulfonate salt by reaction with hexadecyl-p-toluene sulfonate at about 125° C. as the final hexadecyl[2-N-(p-dimethylaminobenzamido)propyl] morpholonium p-toluene sulfonate.

EXAMPLE 4

Preparation of
N-(2-N-Oxazolidinyethyl)-p-dimethylaminobenzamide

The process of Example 1 is repeated except that aminoethyloxazolidine (0.077 mole), ethyldimethylaminobenzoate (0.075 mole) and 0.25 g sodium methylate are used. The final product in a yield of (72%) is N-(2-N-oxazolidinyloethyl)-p-dimethylaminobenzamide in high purity.

EXAMPLE 5

Preparation of Dodecyl-[2-N-(p-dimethylaminobenzamido)ethyl]-Oxazolidinium Bromide 5.3 g of N-(2-N-oxazolidinylethyl)-p-dimethylaminobenzamide (0.022 mole) from Example 4 and 5.0 g of dodecylbromide (0.02 mole) are heated together at 92°–94° C., for 2 hours, Product is crystallized from 80 ml of methylethylketone/methanol (8:1) mixture, The product yield is 86% of theoretical, The following represent some formulations using the sunscreen agents of this invention to illustrate their compatability with a variety of components conventionally employed in such compositions.

EXAMPLE 6

Hair Conditioner and Sunblock

The compound of Example 3 (1.0 wt. %) is premixed with 65.0 wt. % ethanol at room temperature until solution is reached. The following ingredients were then added in the order shown below with mixing between each addition.

| Component | wt. % |
| --- | --- |
| Lauryl lactate (ceraphyl 31) | 1.00 |
| Avocado oil | 0.05 |
| Octyl methoxycinnanamate (Escalol 557) | 1.00 |
| Deionized water | 31.45 |
| Hydrolyzed Animal Protein (Crotein SPO) | 0.25 |

The above formulation increases hair luster while protecting from harmful rays of the sun causing dryness.

EXAMPLE 7

Conditioning Hair Styling Gel and Sunscreen

Crosslinked methyl vinyl ether/maleic anhydride copolymer (6.0 wt. %) was dispersed in 80.2 wt. % of distilled water by mixing for about 45 minutes at about 87° C. The dispersion was then cooled to 60° C. and 0.4 wt. % of sodium hydroxyethyl glycinate followed by 7 wt. of deionized water was added while cooling to room temperature.

A separate mixture of 1 wt. % polyvinylpyrrolidone in 7 wt. % deionized water is prepared at room temperature and a dispersion consisting of 1.0 wt. % compound of Example 2 and 10.0 wt. % of polyethoxylated sorbitan monolaurate (Tween 20) is added with mixing to the aqueous polyvinylpyrrolidone phase at 70° C. The resulting mixture is then added to the crosslinked copolymer phase at 70° C. and mixing continued while cooling to 25° C.

This formulation possesses excellent hair holding power while providing subsequent use as a hair sunscreen.

EXAMPLE 8

Hair Conditioner for Dyed Hair

A dispersion of modified hydroxyethyl cellulose (0.75 wt. %) in 88.03 wt. % deionized water, 1.0 wt. % polyethoxylated sorbitan monolaurate and 0.50 wt. % phenoxyethanol is prepared at 85° C. To this dispersion is gradually added, at about 90° C. a premixed solution of 0.25 wt. % methylparaben, 0.25 wt. % propylparaben in 3.72 wt. % water. After mixing to uniformity, 2.0 wt. % glycol stearate, 1.0 wt. % mink amidopropyl dimethyl-2-hydroxyethyl ammonium chloride, 0.25 wt. % cetyl alcohol, 1.0 wt. % stearyl alcohol, 0.25 wt. % titanium dioxide on mica and 1.0 wt. % of the compound of Example 5 are added in the above order and mixed for 10 minutes and then homogenized for 10 minutes at between about 80°–90° C. The resulting uniform mixture is then cooled to room temperature. This conditioning lotion when applied to dyed hair prevents color fading upon extended exposure to the sun. Substitution of the compound of Example 2 or 3 in the above hair conditioning formulations provides equally good results.

The above products exhibit excellent hair substantivity and protection against harmful rays of the sun. The present products also prevent or minimize color fading of dyed hair and of colored paints and finishes applied to surfaces.

It will be understood that other formulations involving the compounds of this invention provide the benefits described herein and are within the scope of this invention.

What is claimed is:

1. The quaternary ammonium salt of a paradialkylamino benzamide having the formula

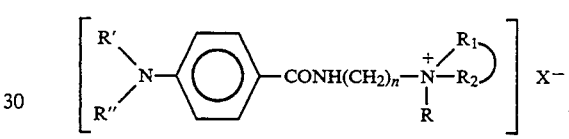

wherein R' and R" are each selected from the group of $C_1$ to $C_2$ alkyl; n is an integer having a value of from 2 to 6; R is an alkyl radical having from 1 to 30 carbon atoms; $R_1$ and $R_2$ together with the attached cationic nitrogen atom forms a 5 to 6-membered heterocyclic ring containing an oxygen atom in addition to the hetero nitrogen atom and said ring is selected from the group of

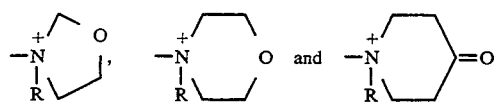

and X is an anion.

2. The quaternary salt of claim 1 wherein n has a value of 2 to 4; R is alkyl having 12 to 18 carbon atoms.

3. The quaternary salt of claim 1 wherein said anion is selected from the group of chloride, bromide sulfate, sulfonate, haloacetal and p-tolyl sulfonate.

4. The quaternary salt of claim 1 wherein said salt is in crystalline form and contains between about 1 and about 8 wt. % moisture.

5. The quaternary salt of claim 1 having the formula

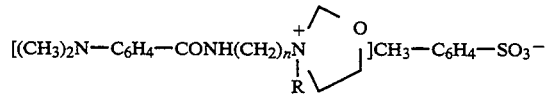

where R is alkyl having from 16 to 18 carbon atoms and n is 2 or 3.

6. The quaternary salt of claim 1 having the formula

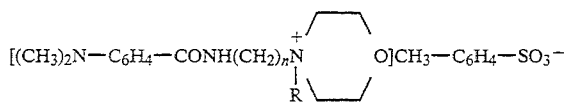

where R is alkyl having from 16 to 18 carbon atoms and n is 2 or 3.

7. The quaternary salt of claim 1 having the formula

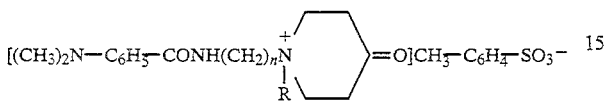

where R is alkyl having from 16 to 18 carbon atoms and n is 2 or 3.

8. A sunscreening composition containing a carrier and an effective sunscreening amount of a quaternary ammonium salt of a para-dialkylamino benzamide of claim 1.

9. The sunscreening composition of claim 8 wherein a mixture of said quaternary ammonium salts of para-dialkylamino benzamides are employed.

10. The sunscreening composition of claim 8 wherein said quaternary salts have the formula

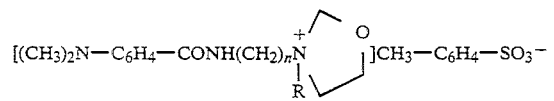

wherein R, in the mixture is alkyl having from 16 to 18 carbon atoms and n is 2 or 3.

11. The sunscreening composition of claim 8 wherein said quaternary salts have the formula

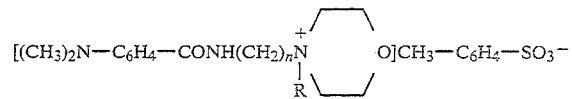

wherein R, in the mixture is alkyl having from 16 to 18 carbon atoms and n is 2 or 3.

12. The sunscreening composition of claim 8 wherein said quaternary salts have the formula

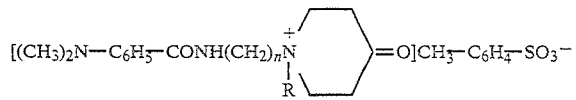

wherein R, in the mixture is alkyl having from 16 to 18 carbon atoms and n is 2 or 3.

13. The sunscreening composition of claim 8 which additionally contains one or more of the components selected from the group of a surfactant, a neutralizer, a stabilizer, a propellant, a coloring agent, a fragrance, a film forming polymer, a preservative, an antistat and a sequestrant.

14. The composition of claim 8 which is in admixture with a conventional hair or skin treating formulation.

15. The composition of claim 8 which is in admixture with a paint formulation.

16. The quaternary salt of claim 8 wherein n has a value of from 2 to 4 and R is alkyl having from 12 to 18 carbon atoms.

* * * * *